(12) United States Patent
Mochizuki

(10) Patent No.: US 6,310,275 B1
(45) Date of Patent: Oct. 30, 2001

(54) ARTIFICIALLY SYNTHESIZED GENE FOR TRYPSIN INHIBITOR

(75) Inventor: Atsushi Mochizuki, Omagari (JP)

(73) Assignee: Director General of Tohoku National Agricultural Experiment Station, Ministry of Agriculture, Forestry and Fisheries, Iwate (JP)

(*) Notice: Subject to any disclaimer, the term of this patent is extended or adjusted under 35 U.S.C. 154(b) by 0 days.

(21) Appl. No.: 09/143,211

(22) Filed: Aug. 28, 1998

(30) Foreign Application Priority Data

Sep. 1, 1997 (JP) .................................................. 9-236332

(51) Int. Cl.[7] ........................... C12N 15/29; C12N 15/82; C12N 15/90; A01H 5/00
(52) U.S. Cl. .................... 800/320.2; 435/69.1; 435/468; 536/23.6; 800/288; 800/302
(58) Field of Search ................................ 435/69.1, 320.3, 435/410, 419, 468; 536/23.6, 23.7; 800/278, 288, 295, 298, 320.2

(56) References Cited

PUBLICATIONS

Johnston et al, Insect Biochem. Molec. Biol. vol. 25, pp. 375–383, 1995.*
Christeller et al, Arch. Insect Biochem. Physiol., vol. 25, pp. 159–173, 1994.*
Rashid et al, Plant Cell Rep., vol. 15, pp. 727–730, 1996.*
Johnson et al, Proc. Natl. Acad. Sci., vol. 86, pp. 9871–9875, 1989.*
Murray et al, Nucl. Acids Res., vol. 17, pp. 477–490, 1989.*
Adang et al, Plant Mol. Biol., vol. 21, pp. 1131–1145, 1993.*
Yamamoto et al, J. Biochem., vol. 94, pp. 849–863, 1983.*
Habu et al, J. Biochem., vol. 111, pp. 249–258, 1992.*

* cited by examiner

Primary Examiner—Gary Benzion
Assistant Examiner—Ashwin Mehta
(74) Attorney, Agent, or Firm—Townsend and Townsend and Crew LLP

(57) ABSTRACT

An artificially synthesized gene encoding a protein having a trypsin inhibitor activity, which is designed so as to be expressed in rice in a stable manner, includes a base sequence encoding an amino acid sequence from Glu at the 1st position to Ser at the 172th position represented in SEQ ID NO: 1 of the Sequence Listing.

5 Claims, 6 Drawing Sheets

FIG. 1

Comparison between amino acid sequence of chymotrypsin inhibitor WCI-3 and amino acid sequence of inhibitor WTI-1B ("|" indicates amino acid sequence having a homology)

```
                                                            60
WCI-3: DDDLVDAEGNLVENGGTYYLLPHIWAHGGGIETAKTGNEPCPLTVVRSPNEVSKGEPIRI
       |  | || || |||||||||  || |||||  | || | ||||||||||||| |||:||
WTI-1B: EPLLDSEGELVRNGGTYYLLPDRWALGGGIEAAATGTETCPLTVVRSPNEVSVGEPLRI
                                                            59
                                                                119
SSQFLSLFIPRGSLVALGFANPPSCAASPWWTVVDSPQGPA-VKLSQQKLPEKDILVFKF
||| | ||| ||| ||||||  || ||||||||||  ||||    |   |   :|||
SSQLRSGFIPDYSLVRIGFANPPKCAPSPWWTVVEDQPQQPSVKLSELKSTKFDY-LFKF
                                                                118
                                                        184
EKVSHSNIHVYKLLYCQHDEEDVKCDQYIGIHRDRNGNRRLVVTEENPLELVLLKAKSETASSH_
|||:     |||: ||| ||      ||| ||  | |||||  ||||
EKVTSKFSS-YKLKYCAKRDTCKD----IGIYRDQKGYARLVVTDENPLVVIFKKVESS_
                                                        173
```

FIG.2

Sequence of artificially synthesized *WTI-1b* gene designed based on base sequence of *WCI-3* gene ATGGGATCCAAAATGAAGAGTACTACATTTCTTGCCCTCTTTCTACTCTCTGCCATCATC
TCACACCTACCATCATCCACTGCTGAGCCATTGCTCGATTCTGAAGGTGAGTTAGTTCGA
AATGGTGGCACATACTATCTGTTGCCAGATAGATGGGCACTCGGGGGAGGAATAGAAGCA
GCAGCAACAGGAACCGAAACATGCCCTCTAACAGTGGTACGATCTCCCAATGAGGTCTCT
GTAGGGGAACCATTAAGGATCTCATCCCAATTGCGTTCAGGGTTCATCCCCGATTACTCT
CTAGTGCGTATTGGATTCGCTAACCCTCCAAAGTGTGCACCTTCTCCGTGGTGGACTGTT
GTTGAGGACCAACCACAACAACCCTCTGTTAAACTTAGTGAGCTAAAATCTACGAAATTC
GATTATCTATTTAAATTCGAGAAAGTTACCTCTAAGTTTTCCTCGTACAAGCTTAAGTAC
TGTGCCAAGAGGGACACCTGTAAGGATATCGGGATTTATAGGGATCAGAAAGGATACGCA
CGTTTGGTGGTGACTGACGAAAACCCATTAGTGGTTATCTTTAAAAAGGTGGAGTCAAGC
TAA

FIG. 3

Sequence of artificially synthesized *WTI-1b* gene obtained by modifying the sequence shown in Figure 1 based on codon usage of genes from Fabaceae plant

ATGGGATCCAAAATGAAGAGTACTACATTTCTTGCCCTCTTTCTACTCTCTGCCATCATC

TCACACCTACCATCATCCACTGCTGAGCCATTGCTCGATTCTGAAGGTGAGTTAGTTCGA

AATGGTGGCACATACTATCTGTTGCCAGATAGATGGGCACTCGGGGGAGGAATAGAAGCA

GCAGCAACAGGAACCGAAACATGCCCTCTAACAGTGGTACGATCTCCCAATGAGGTCTCT

GTAGGGGAACCATTAAGGATCTCATCCCAATTGCGTTCAGGGTTCATCCCCGATTACTCT

CTAGTGCGTATTGGATTCGCTAACCCTCCAAAGTGTGCACCTTCTCCGTGGTGGACTGTT

GTTGAGGACCAACCACAACAACCCTCTGTTAAACTTAGTGAGCTAAAATCTACgAAATTC
↓
T

GATTATCTATTTAAATTCGAGAAAGTTACCTCTAAGTTTTCCTCgTACAAGCTTAAGTAC
↓
A

TGTGCCAAGAGGGACACCTGTAAGGATATCGGGATTTATAGGGATCAGAAAGGATACGCA

CGTTTGGTGGTGACTGACGAAAACCCATTAGTGGTTATCTTTAAAAAGGTGGAGTCAAGC

TAA

FIG. 4

Diagram for showing portions where a sequence "ATTTA" which causes instability of mRNA existed ATGGGATCCAAAATGAAGAGTACTACATTTCTTGCCCTCTTTCTACTCTCTGCCATCATC
TCACACCTACCATCATCCACTGCTGAGCCATTGCTCGATTCTGAAGGTGAGTTAGTTCGA
AATGGTGGCACATACTATCTGTTGCCAGATAGATGGGCACTCGGGGGAGGAATAGAAGCA
GCAGCAACAGGAACCGAAACATGCCCTCTAACAGTGGTACGATCTCCCAATGAGGTCTCT
GTAGGGGAACCATTAAGGATCTCATCCCAATTGCGTTCAGGGTTCATCCCCGATTACTCT
CTAGTGCGTATTGGATTCGCTAACCCTCCAAAGTGTGCACCTTCTCCGTGGTGGACTGTT
GTTGAGGACCAACCACAACAACCCTCTGTTAAACTTAGTGAGCTAAAATCTACTAAATTC
GATTATCTATTtAAATTCGAGAAAGTTACCTCTAAGTTTTCCTCATACAAGCTTAAGTAC
      ↓
      C TGTGCCAAGAGGGACACCTGTAAGGATATCGGGATtTATAGGGATCAGAAAGGATACGCA
            ↓
            C

CGTTTGGTGGTGACTGACGAAAACCCATTAGTGGTTATCTTTAAAAAGGTGGAGTCAAGC
TAA

FIG.6

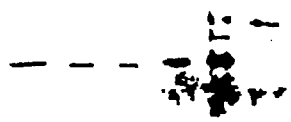

Confirmation for expression levels of trypsin inhibitor in rice genetically engineered with an artificially synthesized gene for trypsin inhibitor by Western blotting Lanes 1, 2 and 3 : 4ng, 2ng, and 1ng of trypsin inhibitor (WTI-1b), respectively
Lanes 4 and 5 : Extracts from genetically engineered rice plants corresponding to clone T10 and clone T33, respectively
Lane 6 : Total protein of extract from non-recombinant rice plant (In each of Lanes 4, 5, and 6, 20μg of total protein was loaded.)

SEQUENCE LISTING

```
<160> NUMBER OF SEQ ID NOS: 18

<210> SEQ ID NO 1
<211> LENGTH: 172
<212> TYPE: PRT
<213> ORGANISM: Psophocarpus tetragonolobus
<220> FEATURE:
<223> OTHER INFORMATION: winged bean Kunitz-type trypsin inhibitor
      WTI-1b

<400> SEQUENCE: 1

Glu Pro Leu Leu Asp Ser Glu Gly Glu Leu Val Arg Asn Gly Gly Thr
 1               5                  10                  15

Tyr Tyr Leu Leu Pro Asp Arg Trp Ala Leu Gly Gly Gly Ile Glu Ala
            20                  25                  30

Ala Ala Thr Gly Thr Glu Thr Cys Pro Leu Thr Val Val Arg Ser Pro
        35                  40                  45

Asn Glu Val Ser Val Gly Glu Pro Leu Arg Ile Ser Ser Gln Leu Arg
    50                  55                  60

Ser Gly Phe Ile Pro Asp Tyr Ser Leu Val Arg Ile Gly Phe Ala Asn
65                  70                  75                  80

Pro Pro Lys Cys Ala Pro Ser Pro Trp Trp Thr Val Val Glu Asp Gln
                85                  90                  95

Pro Gln Gln Pro Ser Val Lys Leu Ser Glu Leu Lys Ser Thr Lys Phe
```

```
                    100              105             110
Asp Tyr Leu Phe Lys Phe Glu Lys Val Thr Ser Lys Phe Ser Ser Tyr
        115                 120             125

Lys Leu Lys Tyr Cys Ala Lys Arg Asp Thr Cys Lys Asp Ile Gly Ile
    130             135             140

Tyr Arg Asp Gln Lys Gly Tyr Ala Arg Leu Val Val Thr Asp Glu Asn
145             150             155                     160

Pro Leu Val Val Ile Phe Lys Lys Val Glu Ser Ser
                165             170

<210> SEQ ID NO 2
<211> LENGTH: 624
<212> TYPE: DNA
<213> ORGANISM: Psophocarpus tetragonolobus
<220> FEATURE:
<221> NAME/KEY: CDS
<222> LOCATION: (1)..(624)
<223> OTHER INFORMATION: winged bean Kunitz chymotrypsin inhibitor 3
      (WCI-3)

<400> SEQUENCE: 2 atg aag agt act aca ttt ctt gcc ctc ttt cta ctc tct gcc atc atc      48
Met Lys Ser Thr Thr Phe Leu Ala Leu Phe Leu Leu Ser Ala Ile Ile
  1               5                  10                  15 tca cac cta cca tca tcc act gct gat gat gat ttg gtc gat gct gaa      96
Ser His Leu Pro Ser Ser Thr Ala Asp Asp Asp Leu Val Asp Ala Glu
             20                  25                  30 ggt aac tta gtt gaa aat ggt ggc aca tac tat ctg ttg cca cat ata     144
Gly Asn Leu Val Glu Asn Gly Gly Thr Tyr Tyr Leu Leu Pro His Ile
         35                  40                  45 tgg gca cac ggg gga gga ata gaa aca gca aaa aca gga aac gaa cca     192
Trp Ala His Gly Gly Gly Ile Glu Thr Ala Lys Thr Gly Asn Glu Pro
     50                  55                  60 tgc cct cta aca gtg gta cga tct ccc aat gag gtc tct aaa ggg gaa     240
Cys Pro Leu Thr Val Val Arg Ser Pro Asn Glu Val Ser Lys Gly Glu
 65                  70                  75                  80 cca ata agg atc tca tcc caa ttc ctt tca ttg ttc atc ccc aga ggc     288
Pro Ile Arg Ile Ser Ser Gln Phe Leu Ser Leu Phe Ile Pro Arg Gly
                 85                  90                  95 tct cta gtg gct ctt gga ttc gct aac cct cca tct tgt gca gct tct     336
Ser Leu Val Ala Leu Gly Phe Ala Asn Pro Pro Ser Cys Ala Ala Ser
            100                 105                 110 ccg tgg tgg act gtt gtt gac tct cca caa gga ccc gct gtt aaa ctt     384
Pro Trp Trp Thr Val Val Asp Ser Pro Gln Gly Pro Ala Val Lys Leu
        115                 120                 125 agt cag caa aaa ctt ccg gaa aag gat att cta gtg ttt aaa ttc gag     432
Ser Gln Gln Lys Leu Pro Glu Lys Asp Ile Leu Val Phe Lys Phe Glu
    130                 135                 140 aaa gtt tcc cat tct aac att cac gtg tac aag ctt ttg tac tgt caa     480
Lys Val Ser His Ser Asn Ile His Val Tyr Lys Leu Leu Tyr Cys Gln
145                 150                 155                 160 cat gac gaa gag gat gtg aag tgt gat cag tat atc ggg att cat agg     528
His Asp Glu Glu Asp Val Lys Cys Asp Gln Tyr Ile Gly Ile His Arg
                165                 170                 175 gat cgc aat gga aac aga cgt ttg gtg gtg act gag gaa aac cca tta     576
Asp Arg Asn Gly Asn Arg Arg Leu Val Val Thr Glu Glu Asn Pro Leu
            180                 185                 190 gag ctt gtg ctt ctg aaa gct aag tca gaa act gca tca agc cat taa     624
Glu Leu Val Leu Leu Lys Ala Lys Ser Glu Thr Ala Ser Ser His
        195                 200                 205
```

<210> SEQ ID NO 3
<211> LENGTH: 207
<212> TYPE: PRT
<213> ORGANISM: Psophocarpus tetragonolobus

<400> SEQUENCE: 3

```
Met Lys Ser Thr Thr Phe Leu Ala Leu Phe Leu Leu Ser Ala Ile Ile
 1               5                  10                  15

Ser His Leu Pro Ser Thr Ala Asp Asp Leu Val Asp Ala Glu
            20                  25                  30

Gly Asn Leu Val Glu Asn Gly Gly Thr Tyr Tyr Leu Leu Pro His Ile
            35                  40                  45

Trp Ala His Gly Gly Gly Ile Glu Thr Ala Lys Thr Gly Asn Glu Pro
     50                  55                  60

Cys Pro Leu Thr Val Val Arg Ser Pro Asn Glu Val Ser Lys Gly Glu
 65                  70                  75                  80

Pro Ile Arg Ile Ser Ser Gln Phe Leu Ser Leu Phe Ile Pro Arg Gly
                 85                  90                  95

Ser Leu Val Ala Leu Gly Phe Ala Asn Pro Pro Ser Cys Ala Ala Ser
                100                 105                 110

Pro Trp Trp Thr Val Val Asp Ser Pro Gln Gly Pro Ala Val Lys Leu
            115                 120                 125

Ser Gln Gln Lys Leu Pro Glu Lys Asp Ile Leu Val Phe Lys Phe Glu
    130                 135                 140

Lys Val Ser His Ser Asn Ile His Val Tyr Lys Leu Leu Tyr Cys Gln
145                 150                 155                 160

His Asp Glu Glu Asp Val Lys Cys Asp Gln Tyr Ile Gly Ile His Arg
                165                 170                 175

Asp Arg Asn Gly Asn Arg Arg Leu Val Val Thr Glu Glu Asn Pro Leu
            180                 185                 190

Glu Leu Val Leu Leu Lys Ala Lys Ser Glu Thr Ala Ser Ser His
        195                 200                 205
```

<210> SEQ ID NO 4
<211> LENGTH: 591
<212> TYPE: DNA
<213> ORGANISM: Artificial Sequence
<220> FEATURE:
<223> OTHER INFORMATION: Description of Artificial Sequence:artificially synthesized gene having trypsin inhibitor activity

<400> SEQUENCE: 4

```
atgaagagta ctacatttct tgccctcttt ctactctctg ccatcatctc acacctacca      60
tcatccactg ctgagccatt gctcgattct gaaggtgagt tagttcgaaa tggtggcaca     120
tactatctgt tgccagatag atgggcactc ggggaggaa tagaagcagc agcaacagga     180
accgaaacat gccctctaac agtggtacga tctcccaatg aggtctctgt aggggaacca     240
ttaaggatct catcccaatt gcgttcaggg ttcatcccg attactctct agtgcgtatt     300
ggattcgcta accctccaaa gtgtgcacct tctccgtggt ggactgttgt tgaggaccaa     360
ccacaacaac cctctgttaa acttagtgag ctaaaatcta ctaaattcga ttatctattc     420
aaattcgaga aagttacctc taagttttcc tcatacaagc ttaagtactg tgccaagagg     480
gacacctgta aggatatcgg gatctatagg gatcagaaag gatacgcacg tttggtggtg     540
actgacgaaa acccattagt ggttatcttt aaaaaggtgg agtcaagcta a              591
```

```
<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence:primer 1

<400> SEQUENCE: 5
gaatttagta gattttagct cactaagttt aacagagggt tgttgtggtt ggtcctcaac      60
aacagtccac cacggagaag                                                  80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence:primer 2

<400> SEQUENCE: 6
ttgcgttcag ggttcatccc cgattactct ctagtgcgta ttggattcgc taaccctcca      60
aagtgtgcac cttctccgtg                                                  80

<210> SEQ ID NO 7
<211> LENGTH: 79
<212> TYPE: DNA
<213> ORGANISM: Artificial Sequence
<220> FEATURE:
<223> OTHER INFORMATION: Description of Artificial Sequence:primer 3

<400> SEQUENCE: 7
cttggcacag tacttaagct tgtatgagga aaacttagag gtaactttct cgaatttgaa      60
tagataatcg aatttagta                                                   79

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence:primer 4

<400> SEQUENCE: 8
atgccctcta acagtggtac gatctcccaa tgaggtctct gtaggggaac cattaaggat      60
ctcatcccaa ttgcgttcag                                                  80

<210> SEQ ID NO 9
<211> LENGTH: 79
<212> TYPE: DNA
<213> ORGANISM: Artificial Sequence
<220> FEATURE:
<223> OTHER INFORMATION: Description of Artificial Sequence:primer 5

<400> SEQUENCE: 9
gtcagtcacc accaaacgtg cgtatccttt ctgatcccta tagatcccga tatccttaca      60
ggtgtccctc ttggcacag                                                   79

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence:primer 6

<400> SEQUENCE: 10
```

```
catactatct gttgccagat agatgggcac tcggggagg aatagaagca gcagcaacag      60
gaaccgaaac atgccctcta                                                80
```

<210> SEQ ID NO 11
<211> LENGTH: 65
<212> TYPE: DNA
<213> ORGANISM: Artificial Sequence
<220> FEATURE:
<223> OTHER INFORMATION: Description of Artificial Sequence:primer 7

<400> SEQUENCE: 11

```
agctgagctc ttagcttgac tccacctttt taaagataac cactaatggg ttttcgtcag    60
tcacc                                                                65
```

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence:primer 8

<400> SEQUENCE: 12

```
atccactgct gagccattgc tcgattctga aggtgagtta gttcgaaatg gtggcacata    60
ctatctg                                                              67
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:primer 9

<400> SEQUENCE: 13

```
atcgagcaat ggctcagcag tggatgatgg                                     30
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer 10

<400> SEQUENCE: 14

```
agcgcccaat acgcaaaccg                                                20
```

<210> SEQ ID NO 15
<211> LENGTH: 603
<212> TYPE: DNA
<213> ORGANISM: Artificial Sequence
<220> FEATURE:
<223> OTHER INFORMATION: Description of Artificial Sequence:artificially
      synthesized WTI-1b gene (mwti1b) designed based on
      base sequence of WCI-3 gene

<400> SEQUENCE: 15

```
atgggatcca aaatgaagag tactacattt cttgccctct ttctactctc tgccatcatc    60
tcacacctac catcatccac tgctgagcca ttgctcgatt ctgaaggtga gttagttcga   120
aatggtggca catactatct gttgccagat agatgggcac tcggggagg aatagaagca   180 gcagcaacag gaaccgaaac atgccctcta acagtggtac gatctcccaa tgaggtctct   240
gtaggggaac cattaaggat ctcatcccaa ttgcgttcag ggttcatccc cgattactct   300
ctagtgcgta ttggattcgc taaccctcca aagtgtgcac cttctccgtg gtggactgtt   360
```

```
gttgaggacc aaccacaaca accctctgtt aaacttagtg agctaaaatc tacgaaattc    420
gattatctat ttaaattcga gaaagttacc tctaagtttt cctcgtacaa gcttaagtac    480
tgtgccaaga gggacacctg taaggatatc gggatttata gggatcagaa aggatacgca    540
cgtttggtgg tgactgacga aaacccatta gtggttatct ttaaaaaggt ggagtcaagc    600
taa                                                                 603
```

<210> SEQ ID NO 16
<211> LENGTH: 603
<212> TYPE: DNA
<213> ORGANISM: Artificial Sequence
<220> FEATURE:
<223> OTHER INFORMATION: Description of Artificial Sequence:artificially
    synthesized WTI-1b gene (mwti1b) obtained by
    modifying the the sequence shown in Figure 1
    (SEQ ID NO:18) based on codon usage of genes
    from Fabaceae plant

<400> SEQUENCE: 16

```
atgggatcca aaatgaagag tactacattt cttgccctct ttctactctc tgccatcatc    60
tcacacctac catcatccac tgctgagcca ttgctcgatt ctgaaggtga gttagttcga    120
aatggtggca catactatct gttgccagat agatgggcac tcggggagg aatagaagca     180 gcagcaacag gaaccgaaac atgccctcta acagtggtac gatctcccaa tgaggtctct    240 gtagggaac cattaaggat ctcatcccaa ttgcgttcag ggttcatccc cgattactct     300
ctagtgcgta ttggattcgc taaccctcca aagtgtgcac cttctccgtg gtggactgtt    360
gttgaggacc aaccacaaca accctctgtt aaacttagtg agctaaaatc tactaaattc    420
gattatctat ttaaattcga gaaagttacc tctaagtttt cctcatacaa gcttaagtac    480
tgtgccaaga gggacacctg taaggatatc gggatttata gggatcagaa aggatacgca    540
cgtttggtgg tgactgacga aaacccatta gtggttatct ttaaaaaggt ggagtcaagc    600
taa                                                                 603
```

<210> SEQ ID NO 17
<211> LENGTH: 603
<212> TYPE: DNA
<213> ORGANISM: Artificial Sequence
<220> FEATURE:
<223> OTHER INFORMATION: Description of Artificial Sequence:artificially
    synthesized WTI-1b gene (mwti1b) as in SEQ ID
    NO:16 where mRNA instability (ATTTA) sequences were modified

<400> SEQUENCE: 17

```
atgggatcca aaatgaagag tactacattt cttgccctct ttctactctc tgccatcatc     60
tcacacctac catcatccac tgctgagcca ttgctcgatt ctgaaggtga gttagttcga    120
aatggtggca catactatct gttgccagat agatgggcac tcgggggagg aatagaagca    180
gcagcaacag gaaccgaaac atgccctcta acagtggtac gatctcccaa tgaggtctct    240
gtaggggaac cattaaggat ctcatcccaa ttgcgttcag ggttcatccc cgattactct    300
ctagtgcgta ttggattcgc taaccctcca aagtgtgcac cttctccgtg gtggactgtt    360
gttgaggacc aaccacaaca accctctgtt aaacttagtg agctaaaatc tactaaattc    420
gattatctat tcaaattcga gaaagttacc tctaagtttt cctcatacaa gcttaagtac    480
tgtgccaaga gggacacctg taaggatatc gggatctata gggatcagaa aggatacgca    540
cgtttggtgg tgactgacga aaacccatta gtggttatct ttaaaaaggt ggagtcaagc    600
```

```
taa                                                            603
```

<210> SEQ ID NO 18
<211> LENGTH: 183
<212> TYPE: PRT
<213> ORGANISM: Psophocarpus tetragonolobus
<220> FEATURE:
<223> OTHER INFORMATION: winged bean Kunitz-type chymotrypsin inhibitor
      3 (WCI-3) amino acid positions 25 through 207

<400> SEQUENCE: 18

```
Asp Asp Asp Leu Val Asp Ala Glu Gly Asn Leu Val Glu Asn Gly Gly
 1               5                  10                  15

Thr Tyr Tyr Leu Leu Pro His Ile Trp Ala His Gly Gly Ile Glu
            20                  25                  30

Thr Ala Lys Thr Gly Asn Glu Pro Cys Pro Leu Thr Val Val Arg Ser
            35                  40                  45

Pro Asn Glu Val Ser Lys Gly Glu Pro Ile Arg Ile Ser Ser Gln Phe
        50                  55                  60

Leu Ser Leu Phe Ile Pro Arg Gly Ser Leu Val Ala Leu Gly Phe Ala
 65                  70                  75                  80

Asn Pro Pro Ser Cys Ala Ala Ser Pro Trp Trp Thr Val Val Asp Ser
                85                  90                  95

Pro Gln Gly Pro Ala Val Lys Leu Ser Gln Gln Lys Leu Pro Glu Lys
                100                 105                 110

Asp Ile Leu Val Phe Lys Phe Glu Lys Val Ser His Ser Asn Ile His
                115                 120                 125

Val Tyr Lys Leu Leu Tyr Cys Gln His Asp Glu Glu Asp Val Lys Cys
        130                 135                 140

Asp Gln Tyr Ile Gly Ile His Arg Asp Arg Asn Gly Asn Arg Arg Leu
145                 150                 155                 160

Val Val Thr Glu Glu Asn Pro Leu Glu Leu Val Leu Leu Lys Ala Lys
                    165                 170                 175

Ser Glu Thr Ala Ser Ser His
                180
```

ARTIFICIALLY SYNTHESIZED GENE FOR TRYPSIN INHIBITOR

BACKGROUND OF THE INVENTION

1. Field of the Invention

The present invention relates to an artificially synthesized gene encoding an active protein. More specifically, the present invention relates to an artificially synthesized gene encoding a protein having a trypsin inhibitor activity. The present invention also relates to a plant which expresses a gene encoding a protein having trypsin inhibitor activity, which also confers resistance to lepidopteran insect pests.

2. Description of the Related Art

There exist several protease inhibitors including trypsin inhibitors in Fabaceae plant (Yamamoto et al. *J. Biochem.* 94, pp. 849–863, 1983).

The trypsin inhibitors derived from Fabaceae plant are classified into two groups on the basis of their molecular weight and cystine content. One is the Bowman-Birk type inhibitors which have molecular weights of around 8,000 and are characterized by a high cystine content, namely seven disulfide bridges (Norioka et al., *J. Biochem.* 94, pp. 589–599). The other is the Kunitz type inhibitors which have molecular weights of around 20,000 and include two disulfide bridges (Shibata et al., *J. Biochem.* 99: pp. 1147–1155, 1986). The Kunitz type inhibitors are known to exist not only in Fabaceae plant but also in soybean, silk tree, barley, acacia, and rice (Yamamoto et al. *J. Biochem.* 94, pp. 849–863, 1983). Trypsin inhibitors are present in the pancreas and plasma of vertebrates as peptides which can inhibit the activity of the digestive enzyme, trypsin. Although the role of the trypsin inhibitor in a plant is not known very well, it has been reported that a trypsin inhibitor ingested by an insect inhabits growth of the insect (R. Johnson et al., *Proc. Natl. Acad. Sci. USA* 86, pp. 9871–9875, 1989).

A trypsin inhibitor WTI-1b derived from the winged bean (*Psophocarpus tetragonolobus* (L.) DC.) is a Knitz type inhibitor which has molecular weight of 19,200, and the complete amino acid sequence of the purified protein has been identified (Yamamoto et al. *J. Biochem.* 94, pp. 849–863, 1983). A gene encoding the WTI-1b has not been isolated.

SUMMARY OF THE INVENTION

According to one aspect of this invention, an artificially synthesized gene encoding a protein having a trypsin inhibitor activity, which is designed so as to be expressed in rice in a stable manner, includes a base sequence encoding an amino acid sequence from Glu at the 1st position to Ser at the 172th position represented in SEQ ID NO 1 of the Sequence Listing or a base sequence encoding an amino acid sequence in which one or more amino acids are subjected to deletion, substitution, or addition in the amino acid sequence. The gene is designed by the steps of: (a) determining a plurality of amino acid pairs by comparing an amino acid sequence of a trypsin inhibitor with an amino acid sequence of a chymotrypsin inhibitor derived from a plant, wherein each of the amino acid pairs consists of a first amino acid from the amino acid sequence of the trypsin inhibitor and a second amino acid from the amino acid sequence of the chymotrypsin inhibitor; (b) selecting a codon for an amino acid from each of the plurality of amino acid pairs, wherein when the first amino acid and the second amino acid in the amino acid pair are identical to each other, a codon for the second amino acid is selected; and when the first amino acid and the second amino acid in the amino acid pair are different from each other, a codon for the first amino acid is selected so as to be similar to the codon of the second amino acid; (c) obtaining a first base sequence by positioning the selected plurality of codons along the amino acid sequence of the trypsin inhibitor; (d) obtaining a second base sequence by replacing a codon for an amino acid having low codon usage in the first base sequence with a codon for an amino acid having a high codon usage; and (e) obtaining a base sequence of interest by modifying a sequence which causes instability of mRNA in the second base sequence so as not to change an amino acid sequence encoded by the second sequence.

In one embodiment of the present invention, the amino acid sequence of the trypsin inhibitor is an amino acid sequence of a trypsin inhibitor derived from winged bean.

In another embodiment of the present invention, the amino acid sequence of the trypsin inhibitor derived from winged bean is an amino acid sequence of WTI-1b protein.

In still another embodiment of the present invention, the amino acid sequence of the chymotrypsin inhibitor derived from the plant is an amino acid sequence of a chymotrypsin inhibitor derived from winged bean.

In still yet another embodiment of the present invention, the amino acid sequence of the chymotrypsin inhibitor derived from winged bean is an amino acid sequence of WCI-3.

In still yet another embodiment of the present invention, a base sequence encoding a processing region positioned at 5' side of the gene is further included.

In still yet another embodiment of the present invention, the processing region is an amino acid sequence from Met at the 1st position to Ala at the 24th position represented in SEQ ID NO:3 of the Sequence Listing.

In still yet another embodiment of the present invention, the artificially synthesized gene consists of a base sequence represented by SEQ ID NO:4 of the Sequence Listing.

According to another aspect of this invention, in a plant, an artificially synthesized gene according to claim 1 is introduced. An expression vector comprising (i) an expression cassette containing the artificially synthesized gene which is operably liked to a plant promoter, and (ii) a selectable marker gene is introduced in the plant.

Thus, the invention described herein makes possible the advantages of (1) providing a method for designing a useful gene which is expressed in high efficiency in a useful plant; and (2) providing means for conferring a new character on a useful plant. More specifically, the objective of the present invention is the expression of a trypsin inhibitor in a useful plant such as rice by the genetic engineering. To the extent that the inventor is aware of, prior to the filing of Japanese Patent application NO:9–236332, on which the present application claims priority, there were no reports on examples where an artificially synthesized gene encoding a protein from a Fabaceae plant was highly expressed in higher plant, conferring a new character thereto.

These and other advantages of the present invention will become apparent to those skilled in the art upon reading and understanding the following detailed description with reference to the accompanying figures.

BRIEF DESCRIPTION OF THE DRAWINGS

FIG. 1 is a sequence alignment showing a comparison between the amino acid sequence of WTI-1b (SEQ ID NO:1) and the amino acid sequence of WCI-3 (SEQ ID NO:18).

FIG. 2 shows a sequence of an artificially synthesized gene (mwti1b) (SEQ ID NO:15) for WTI-1b which was designed based on a base sequence for WCI-3.

FIG. 3 shows a sequence of an artificially synthesized gene (mwti1b) for WTI-1b obtained by modifying the sequence shown in FIG. 1 based on codon usage of genes from Fabaceae plant (SEQ ID NO:16). The modified portions are indicated by underlines. A base before the modification is denoted by a small letter, and a base after the modification is denoted by a capital letter.

FIG. 4 is a diagram for showing portions where a sequence "ATTTA" which may cause instability of mRNA existed. Modified portions are indicated by underlines and the modified sequence is presented as SEQ ID NO:17. A base before the modification is denoted by a small letter, and a base after the modification is denoted by a capital letter.

FIG. 6 shows the result of Western blotting for analyzing expression levels of the trypsin inhibitor in rice genetically engineered with the artificially synthesized gene encoding trypsin inhibitor.

DESCRIPTION OF THE PREFERRED EMBODIMENTS

Figure 5:
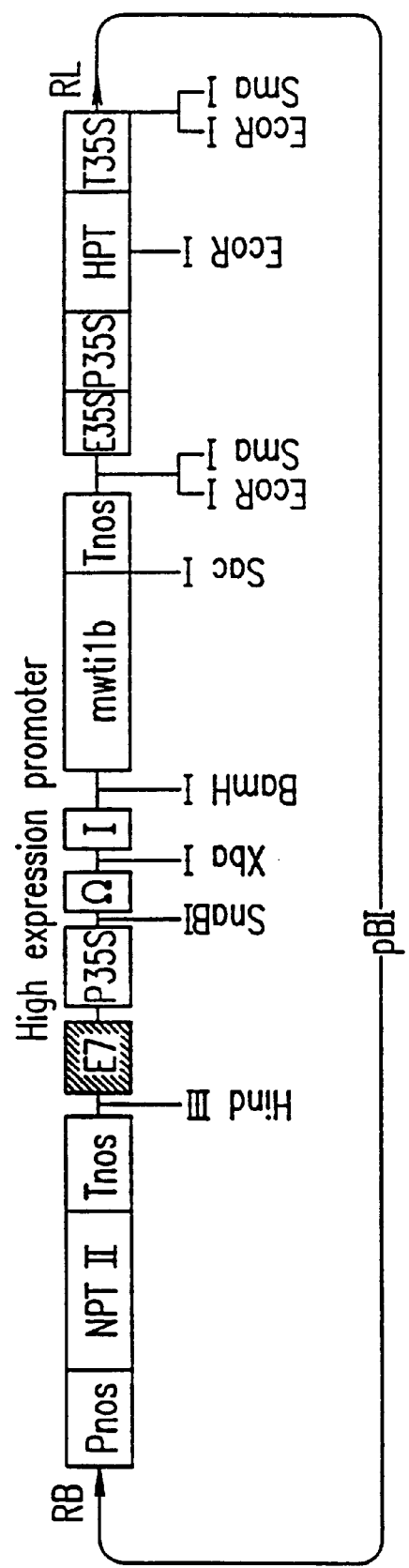
FIG. 5 is a schematic diagram showing a structure of vector construct of pMLH7133mwti1b.

Hereinafter, the present invention will be described in detail.

The gene of the present invention is an artificially synthesized gene which is designed utilizing a DNA database. The term "artificially synthesized gene" as used herein refers to a base sequence designed by imitating a naturally occurring gene so as to be expressed in a stable and efficient manner. As the aforementioned DNA database, GenBank, EMBL, DDBJ, or the like known to those skilled in the art may be used. A plant gene in these databases is subject to design of an artificially synthesized gene by analyzing it utilizing a gene analysis application. As the gene analysis application, GENETYX-Mac or the like is known to those skilled in the art.

The term "plant gene" as used herein substantially refers to a useful gene derived from monocotyledon, dicotyledon, or the like. Although a plant gene encoding a protein having a trypsin inhibitor activity is exemplified in this specification as a preferable example of a plant gene, the plant gene is not limited thereto. The term "protein having a trypsin inhibitor activity" refers to a trypsin inhibitor, or a protein having an activity functionally equivalent to that of the trypsin inhibitor. The protein having an activity inhibiting a trypsin can be considered to be functionally equivalent to the trypsin inhibitor.

Hereinafter, the present invention will be described by way of illustrative examples.

According to one embodiment of the present invention, first, an amino acid sequence of a trypsin inhibitor is compared with an amino acid sequence of a chymotrypsin inhibitor whose cDNA has already been known derived from the same plant. By comparing these two amino acid sequences each other, a homologous region between the two amino acid sequences is determined. Subsequently, from the amino acid sequences positioned in the determined homologous region, pairs of homologous amino acids (i.e., pairs of the identical amino acids) and pairs of non-homologous amino acids in the homologous region or an non-homologous region (i.e., pairs of different amino acids) are determined. An amino acid selected from the amino acid sequence of the trypsin inhibitor is named a first amino acid. An amino acid selected from the amino acid sequence of the chymotrypsin inhibitor is named a second amino acid. Herein, a plurality of pairs of amino acids containing the first amino acid from the amino acid sequence of the trypsin inhibitor and the second amino acid from the amino acid sequence of the chymotrypsin inhibitor are sequentially determined in accordance with the amino acid sequence of the trypsin inhibitor or that of the chymotrypsin inhibitor.

Subsequently, a first base sequence is designed from the thus obtained plurality of amino acid pairs. A codon for the homologous amino acid of the chymotrypsin inhibitor gene is selected from the pair of the homologous amino acids. A codon for the trypsin inhibitor amino acid (i.e., the first amino acid), which is similar to the codon for the chymotrypsin inhibitor amino acid (i.e., the second amino acid) is selected from the pair of the non-homologous amino acids. The term "similar codons" as used herein refers to, for example, codons having at least the same first base in the codon. Herein, the number of nucleic acid codons corresponding to the number of the amino acids from the N-terminal to the C-terminal of the amino acid sequence of the trypsin inhibitor may be selected. The number of codons to be selected is determined by taking the activity of the protein to be encoded into consideration.

Next, the plurality of selected codons are positioned along the amino acid sequence of the trypsin inhibitor, thereby obtaining the first base sequence.

Thereafter, the codon having low codon usage in the first base sequence is replaced with its synonym codon having a high codon usage, thereby obtaining a second base sequence.

As can be appreciated by those skilled in the art, the synonym codons encoding the same amino acid are not used equally, and particular codons are more likely to be used. The usage of a particular codon in particular species of organism is calculated by obtaining the codon usage in each of the genes expressed in this species of organism, and then averaging the obtained values. The term "codon having low codon usage" as used herein refers to a codon having the codon usage of, for example, 10% or less in certain species of organism, wherein the codon usage is obtained by the calculation on the basis of the information from the aforementioned DNA database. The term "codon having a high codon usage" as used herein refers to a codon, for example, having the codon usage of more than 10%, wherein the codon usage is obtained by the calculation on the basis of the information from the aforementioned DNA database. Each of Tables 1A to 1C shows the codon usage used in designing the artificially synthesized gene of this invention. The codon usages are of Fabaceae plant (i.e., Glycine, Phaseolus, and Pisum). Not only the codon usage of Fabaceae plant, but the codon usage of any species of organism may be used. Preferably, the codon usage in species of organism which may be used for expressing the protein encoded by the artificially synthesized gene, or the codon usage in species of organism into which the artificially synthesized gene may be introduced is preferably used.

The following tables 1A to 1C are of codon usages of a major Fabaceae plant.

TABLE 1A

Glycine max [gbpln]: 314 CDS's (117949 codons)

fields: [triplet] [frequency: per thousand] ([number])

| | | | | | | | | | | | | | | | |
|---|---|---|---|---|---|---|---|---|---|---|---|---|---|---|---|
| Phe | UUU | 20.1 | (2372) | Ser | UCU | 16.7 | (1965) | Tyr | UAU | 16.8 | (1979) | Cys | UGU | 7.0 | (822) |
| Phe | UUC | 20.3 | (2400) | Ser | UCC | 11.4 | (1346) | Tyr | UAC | 15.7 | (1857) | Cys | UGC | 7.2 | (854) |
| Leu | UUA | 8.0 | (946) | Ser | UCA | 13.6 | (1604) | Och | UAA | 1.1 | (126) | Opa | UGA | 1.0 | (116) |
| Leu | UUG | 21.5 | (2533) | Ser | UCG | 4.5 | (535) | Amb | UAG | 0.6 | (73) | Trp | UGG | 11.7 | (1384) |
| Leu | CUU | 23.1 | (2721) | Pro | CCU | 20.7 | (2437) | His | CAU | 13.4 | (1575) | Arg | CGU | 7.5 | (881) |
| Leu | CUC | 15.7 | (1847) | Pro | CCC | 10.0 | (1178) | His | CAC | 10.8 | (1274) | Arg | CGC | 6.8 | (799) |
| Leu | CUA | 7.9 | (927) | Pro | CCA | 22.4 | (2639) | Gln | CAA | 21.3 | (2516) | Arg | CGA | 4.0 | (476) |
| Leu | CUG | 11.5 | (1362) | Pro | CCG | 4.1 | (483) | Gln | CAG | 18.3 | (2156) | Arg | CGG | 3.0 | (357) |
| Ile | AUU | 25.2 | (2974) | Thr | ACU | 17.9 | (2115) | Asn | AAU | 20.7 | (2440) | Ser | AGU | 12.2 | (1443) |
| Ile | AUC | 16.4 | (1930) | Thr | ACC | 15.5 | (1834) | Asn | AAC | 22.9 | (2704) | Ser | AGC | 10.9 | (1280) |
| Ile | AUA | 12.4 | (1466) | Thr | ACA | 14.6 | (1718) | Lys | AAA | 26.0 | (3069) | Arg | AGA | 14.3 | (1690) |
| Met | AUG | 22.2 | (2620) | Thr | ACG | 3.7 | (438) | Lys | AAG | 38.7 | (4562) | Arg | AGG | 13.2 | (1558) |
| Val | GUU | 25.9 | (3051) | Ala | GCU | 28.0 | (3304) | Asp | GAU | 34.0 | (4015) | Gly | GGU | 21.9 | (2580) |
| Val | GUC | 12.0 | (1421) | Ala | GCC | 16.9 | (1990) | Asp | GAC | 20.6 | (2428) | Gly | GGC | 13.4 | (1586) |
| Val | GUA | 7.2 | (854) | Ala | GCA | 22.8 | (2694) | Glu | GAA | 34.7 | (4098) | Gly | GGA | 22.2 | (2617) |
| Val | GUG | 22.2 | (2622) | Ala | GCG | 5.5 | (652) | Glu | GAG | 35.8 | (4220) | Gly | GGG | 12.2 | (1436) |

Coding GC 46.27% 1st letter GC 53.58% 2nd letter GC 39.69% 3rd letter GC 45.54%

TABLE 1B

*Phaseolus vulgaris* [gbpln]: 89 CDS's (31434 codons)

fields: [triplet] [frequency: per thousand] ([number])

| | | | | | | | | | | | |
|---|---|---|---|---|---|---|---|---|---|---|---|
| UUU | 16.4 | (514) | UCU | 22.8 | (718) | UAU | 13.5 | (425) | UGU | 4.8 | (151) |
| UUC | 25.8 | (812) | UCC | 20.0 | (630) | UAC | 20.5 | (645) | UGC | 7.7 | (242) |
| UUA | 6.7 | (212) | UCA | 13.8 | (433) | UAA | 0.6 | (20) | UGA | 1.2 | (39) |
| UUG | 18.0 | (567) | UCG | 4.8 | (152) | UAG | 1.0 | (30) | UGG | 12.3 | (388) |
| CUU | 21.7 | (682) | CCU | 20.1 | (631) | CAU | 10.7 | (336) | CGU | 6.3 | (199) |
| CUC | 17.7 | (556) | CCC | 12.9 | (407) | CAC | 12.5 | (392) | CGC | 5.4 | (171) |
| CUA | 7.2 | (227) | CCA | 20.0 | (628) | CAA | 17.4 | (546) | CGA | 2.7 | (86) |
| CUG | 13.1 | (412) | CCG | 4.5 | (142) | CAG | 16.4 | (516) | CGG | 2.4 | (77) |
| AUU | 18.1 | (568) | ACU | 15.7 | (492) | AAU | 20.3 | (638) | AGU | 10.5 | (329) |
| AUC | 21.3 | (670) | ACC | 19.1 | (601) | AAC | 32.7 | (1028) | AGC | 14.4 | (452) |
| AUA | 9.3 | (292) | ACA | 12.8 | (402) | AAA | 26.2 | (823) | AGA | 10.8 | (341) |
| AUG | 19.8 | (622) | ACG | 6.7 | (210) | AAG | 34.6 | (1088) | AGG | 11.8 | (371) |
| GUU | 24.0 | (753) | GCU | 27.1 | (851) | GAU | 26.9 | (846) | GGU | 27.5 | (865) |
| GUC | 12.9 | (405) | GCC | 21.5 | (676) | GAC | 23.3 | (733) | GGC | 15.9 | (499) |
| GUA | 5.7 | (180) | GCA | 18.3 | (576) | GAA | 27.9 | (876) | GGA | 27.7 | (871) |
| GUG | 25.0 | (787) | GCG | 5.5 | (172) | GAG | 32.4 | (1020) | GGG | 13.1 | (411) |

Coding GC 48.38% 1st letter GC 52.58% 2nd letter GC 42.03% 3rd letter GC 50.53%

TABLE 1C

*Pisum sativum* [gbpln]: 295 CDS's (103967 codons)

fields: [triplet] [frequency: per thousand] ([number])

| | | | | | | | | | | | |
|---|---|---|---|---|---|---|---|---|---|---|---|
| UUU | 23.0 | (2387) | UCU | 21.6 | (2249) | UAU | 17.4 | (1808) | UGU | 7.9 | (820) |
| UUC | 17.8 | (1854) | UCC | 10.2 | (1059) | UAC | 12.5 | (1296) | UGC | 5.6 | (585) |
| UUA | 9.8 | (1014) | UCA | 16.5 | (1716) | UAA | 1.3 | (135) | UGA | 0.9 | (92) |
| UUG | 22.9 | (2378) | UCG | 4.8 | (498) | UAG | 0.6 | (65) | UGG | 10.5 | (1090) |
| CUU | 25.5 | (2655) | CCU | 19.2 | (1991) | CAU | 13.5 | (1408) | CGU | 9.0 | (938) |
| CUC | 12.6 | (1307) | CCC | 5.3 | (555) | CAC | 7.8 | (815) | CGC | 4.3 | (448) |
| CUA | 7.6 | (793) | CCA | 17.9 | (1856) | CAA | 19.6 | (2034) | CGA | 4.1 | (424) |
| CUG | 8.0 | (830) | CCG | 4.9 | (510) | CAG | 12.8 | (1328) | CGG | 2.5 | (265) |

TABLE 1C-continued

Pisum sativum [gbpln]: 295 CDS's (103967 codons)

fields: [triplet] [frequency: per thousand] ([number])

| AUU | 29.3 | (3046) | ACU | 22.5 | (2339) | AAU | 23.8 | (2470) | AGU | 13.8 | (1430) |
|-----|------|--------|-----|------|--------|-----|------|--------|-----|------|--------|
| AUC | 16.4 | (1704) | ACC | 13.6 | (1415) | AAC | 19.8 | (2054) | AGC | 8.8  | (910)  |
| AUA | 11.5 | (1193) | ACA | 16.8 | (1750) | AAA | 30.7 | (3187) | AGA | 16.1 | (1678) |
| AUG | 20.5 | (2133) | ACG | 3.7  | (389)  | AAG | 37.8 | (3930) | AGG | 11.1 | (1154) |
| GUU | 33.1 | (3445) | GCU | 35.8 | (3720) | GAU | 38.9 | (4048) | GGU | 30.1 | (3131) |
| GUC | 10.3 | (1068) | GCC | 12.3 | (1281) | GAC | 16.4 | (1707) | GGC | 10.0 | (1039) |
| GUA | 9.0  | (932)  | GCA | 22.7 | (2362) | GAA | 37.1 | (3862) | GGA | 27.8 | (2889) |
| GUG | 17.3 | (1803) | GCG | 5.6  | (581)  | GAG | 30.8 | (3205) | GGG | 8.7  | (909)  |

Coding GC 43.72% 1st letter GC 52.07% 2nd letter GC 40.47% 3rd letter GC 38.63%

Next, in the case where a sequence which may cause the instability of mRNA exists in the aforementioned second base sequence, such a sequence may be modified so as not to change the amino acid sequence encoded by the second base sequence. As a result, a base sequence of interest is obtained. In eucaryote, especially in monocotyledon such as rice and maize, it is known that the sequence "ATTA" may cause the instability of mRNA after transcription of a gene (see Ohme-Takagi et al., *Proc. Natl. Acad. Sci. USA*., Vol. 90, pp. 11811–11815, 1993).

Occasionally, a known base sequence having a particular function may be positioned in the thus obtained base sequence of interest. Examples of such a base sequence include a base sequence encoding a processing region which transports a protein precursor to a vacuole.

The thus obtained base sequence of interest may be synthesized using a method known to those skilled in the art such as a Polymerase chain reaction (hereinafter, referred to simply as "PCR") method. Preferably, the base sequence of interest may be synthesized by using a long chain DNA synthesizing method utilizing PCR (the production of the synthetic DNA is described in Plant Cell Technology Series 2, "PCR Experimental Protocol for Plant" in *Cell Technology*, Supp., compiled under the supervision of Ko Shimamoto and Takuji Sasaki, SHUJUNSHA Co., Ltd., published in Apr. 10, 1995). According to this method, DNA is synthesized using only long synthetic oligonucleotide primers. A pair of primers are synthesized so as to have a complement chain or an overlap of about 10 to 12 mer at 3'-terminal, respectively, and DNA synthesis is performed using each of the primers as a template. The full length of the primer is preferably in the range from about 100 to 60 mer.

Practically, the base sequence of interest is divided into a plurality of about 400 base pair (bp) segments as needed. Then, about 6 or less long primers are synthesized so as to cover the base sequence of interest or each of the segments of interest. Using the primers, the base sequence of interest or the segment of interest is then synthesized.

First, a pair of primers designed based on a base sequence in a central region of the base sequence of interest or the segment of interest is synthesized, and PCR is then performed using the pair of primers.

Second, using the resulting PCR product as a template, PCR is performed. Briefly, two primers for extending the base sequence are synthesized so as to respectively overlap by 10 to 12 mer at the 3' side of the template, and PCR is then performed using the template and the primers. This operation is repeated to extend the base sequence, thereby obtaining a base sequence of interest or segments of interest. Optionally, restriction sites are respectively provided at both ends of each of the segments of interest or the base sequence of interest, and the base sequence or the segment is introduced into a cloning vectors in accordance with a conventional method. The thus obtained cloned base sequence is sequenced by a DNA-sequencer using a conventional method to confirm whether the base sequence of interest is obtained.

PCR is known to those skilled in the art, and those skilled in the art may appropriately select a reactive solution and a reaction cycle to be used in PCR. For example, see "PCR Experimental Protocol for Plant", compiled under the supervision of Ko Shimamoto and Takuji Sasaki, SHUJUNSHA Co., Ltd.)

For example, PCR is performed as follows.
1. Reagent:
(1) Primer synthesis

An adjusted reagent suitable for a machine to be employed (e.g., Model 391 manufactured by Perkin-Elmer) is used in accordance with the manufacturer's instructions.
(2) PCR reaction A reagent suitable for a machine to be employed (e.g., Program Temp. Control System PC-700 (manufactured by ASTEC Co., Ltd.) is used.
(3) DNA sequencing A kit suitable for a machine to be employed (e.g., Model 373A manufactured by Perkin-Elmer) is used.
2. Primer Synthesis:

A primer is synthesized using a DNA synthesizer, for example, by β-cyanoethyl phosphoamidites method.
3. Production of Double Stranded Segment by PCR:

As a heat-resistant DNA synthetic enzyme, AmpliTaq DNA polymerase (manufactured by Perkin-Elmer), for example, is used at a $Mg^{2+}$ concentration of 1.5 milli molar (mM), and synthesis is performed with the following reaction system.

TABLE 2

| Temperature | Time (min.) | The number of cycles |
|-------------|-------------|----------------------|
| 94          | 2.0         | 1                    |
| 37          | 10.0        | 1                    |
| 94          | 0.5         | 30                   |

TABLE 2-continued

| Temperature | Time (min.) | The number of cycles |
|---|---|---|
| 55 | 0.5 | |
| 72 | 2.0 | |

The thus obtained artificially synthesized gene is operably linked to a plant gene promoter, and then introduced into a plant host such as rice in accordance with a conventional method, e.g., Agrobacterium binary vector method (Hiei et al., 1994, *Plant J*. 6: pp. 271–28).

The term "plant promoter" as used herein refers to a promoter of a gene which expresses in a plant. Examples of the plant promoter include, but are not limited to, the Cauliflower mosaic virus 35S promoter (hereinafter, referred to as "CaMV 35S promoter"), the promoter of nopaline synthase, and the like. An enhancer can be used for high expression. As the enhancer, an enhancer region containing a sequence upstream of the CaMV 35S promoter is preferably used. Several enhancers may be used.

The term "expression cassette" as used herein refers to a nucleic acid sequence in which the recombinant gene and various regulator elements regulating the expression of the recombinant gene, e.g., a promoter, an enhancer, and the like are operably linked to each other in a host cell in such a manner that the recombinant gene may be expressed. The expression cassette may be constructed in accordance with a conventional method. An appropriate promoter, e.g., the E7-P35S-Ω-In promoter is linked to the recombinant gene. The E7-P35S-Ω-In promoter is known to be inducible and expressed at a high level in a rice plant (see Mitsuhara et al., *Plant Cell Physiol*. 37 (1): pp. 49–59, 1996). More preferably, a terminator can be linked to the recombinant gene.

The term "terminator" as used herein refers to a sequence positioned downstream of a region of a gene encoding a protein, which is involved in the termination of transcription of DNA into mRNA and the addition of a poly A sequence. The terminator is known to be involved in the stability of mRNA and thereby affect the expression level of a gene. Although not limited, examples of the terminator include a CaMV 35S terminator, and a terminator of the nopaline synthase gene.

The term "expression vector" as used herein refers to a vehicle transferring the expression cassette to a host cell. It is well-known to those skilled in the art that the type of an expression vector and the kind of a regulator element to be used may vary depending upon a host cell. The expression vector of the present invention can further have a T-DNA region and a selectable marker gene.

It is desirable that the selectable marker gene enables a transgenic plant to be easily selected. As the selectable marker gene, the neomycin phosphotransferase II (NPTII) gene, a hygromycin B phosphotransferase (HPT) gene, or the like may preferably be used.

Although not limited thereto, examples of the promoter expressing the selectable marker gene include the above-mentioned plant promoters such as the CaMV 35S promoter, and the nopaline synthase promoter. Among the CaMV 35S promoters which are constitutively expressed at a high level, a promoter of the combination of E35S and P35S, in particular, may preferably be used.

As a vector used for constructing an expression vector, a pBI-type vector, a pUC-type vector, or a pTRA-type vector may be preferably used. The pBI-type vector can introduce an expression cassette into a plant via Agrobacterium using a binary vector-system or intermediate vector-system. Examples of the pBI-type vector include pBI121, pBI101, pBI101.2, pBI101.3, and the like. The pUC-type vector may introduce an expression cassette directly into a plant. Examples of the pUC-type vector include pUC18, pUC19, pUC9, and the like. Herein, pBI121 in GUS Fusion System (Clontech) which is a PBI-type binary vector may preferably be used. This expression vector includes an expression cassette containing (i) a fusion gene at a region (T-region) which may be introduced into a plant, and (ii) the NPTII gene which is expressed under the control of the nopaline synthase promoter as a marker gene.

Methods known to those skilled in the art may be used for introducing a recombinant gene, an expression cassette, or an expression vector into a plant cell.

The expression cassette or the expression vector obtained in the above-described manner is introduced into a cell using the Agrobacterium method or the directly introducing method.

As the method using Agrobacterium, for example, a method of Nagel et al. (Microbiol. Lett., 67, 325, 1990) can be used. According to this method, for example, Agrobacterium is first transformed with an expression vector by electroporation, and then the transformed Agrobacterium is introduced into a plant cell by a method described in *Plant Molecular Biology Manual* (S.B. Gelvin et al., Academic Press Publishers). As the method for directly introducing an expression cassette or an expression vector into a cell, an electroporation method and a gene gun method may suitably be used.

The cells, into which an expression cassette or an expression vector is introduced, are then subjected to a selection process based on drug resistance such as a hygromycin resistance. Thereafter, the cells can be regenerated as a plant by a conventional method.

In order to confirm the expression of a foreign gene in the transgenic plant, a method known to those skilled in the art may be used. For example, a method of detecting a protein encoded by the gene may be used. A soluble protein can be extracted from the transgenic plant; and the extracted protein is separated by SDS-PAGE (sodium dodecyl sulfate polyacrylamide gel electrophoresis) as described in *Analytical Biochemistry* 166, pp. 368–379, transferred to a PVDF membrane, and reacted with an antiserum against the protein of interest. Then, the resulting band is immunochemically detected, thereby confirming the expression of the protein.

Alternatively, the activity of the foreign gene product may be directly measured by resistance against a harmful insect. For example, newly hatched larvae of a harmful insect are allowed to ingest a leaf of the transgenic plant. After an appropriate period of time passed therefrom, the weight of the larva is measured, thereby confirming the activity of the foreign gene product. An example of the harmful insect includes a lepidopteran insect.

Hereinafter, the present invention will be further described in detail by way of illustrative examples. A restriction enzyme, a plasmid, and the like used in the following examples are available from Takara Shuzo Co., Ltd. and Toyobo Co., Ltd.

EXAMPLE 1

Designing of an Artificially Synthesized Gene Encoding a Protein Having the Activity of a Trypsin Inhibitor (WTI-1b) Derived From the Winged Bean In order to design the artificially synthesized gene encoding the protein having the activity of the trypsin inhibitor (WTI-1b) derived from the winged bean (*Psophocarpus* tetragonolobus (L.) DC.), cDNA sequence for the chymotrypsin inhibitor (WCI-3) derived from the winged bean (*Psophocarpus tetragonolobus* (L.) DC.), which has a high homology with WTI-1b in the amino acid sequence, was utilized (Peyachoknagul et al., *Plant Molecular Biology* 12:51–58 (1989)). As the amino acid sequence of WTI-1b, the sequence presented by Yamamoto et al. (*J. Biochem*. 94, pp. 849–863, 1983) was used. The cDNA sequence for WCI-3 was obtained from the DNA databases of GenBank, EMBL, and DDBJ. The amino acid sequence of WTI-1b was aligned with the amino acid sequence of WCI-3, and homologous regions were determined utilizing the gene analysis application GENETYX-Mac. Based on the homologous regions of the aligned two sequences, the amino acid sequence of WTI-1b was associated with the amino acid sequence of WCI-3, thereby obtaining a plurality of amino acid pairs consisting of the amino acid from WTI-1b and the amino acid from WCI-3 (shown in FIG. 1). Next, from each of the pairs of the homologous amino acids obtained from WTI-1b and WCI-3, the same codons as that used in the gene for WCI-3 were selected. From pairs of non-homologous amino acids, codons were selected so as to have a fewer number of different bases from the base sequence in the WCI-3 gene (FIG. 2).

The known codon usage of Fabaceae plant was searched using a DNA database (e.g., GenBank, EMBL, DDBJ, or the like). Then, of the codons of the artificially synthesized gene for WTI-1b designed above, codons having low usage in Fabaceae plant were replaced by codons having high usage (FIG. 3).

In the gene sequence shown in FIG. 3, since there existed two portions of "ATTTA" sequence which may cause the instability of mRNA after the gene transcripted in rice, the portions were modified so as not to change the amino acids encoded thereby (FIG. 4).

Furthermore, the cDNA of WCI-3 has a processing region consisting of a hydrophilic peptide at the 5' side (i.e., the amino acid sequence from Met at the $1^{st}$ position to Ala at the $24^{th}$ position represented in SEQ ID NO:3 of the Sequence Listing). The region is utilized for transporting a protein precursor to a vacuole after translation. A base sequence the same as this sequence (i.e., the nucleotide base sequence from A at the $1^{st}$ position to T at the $72^{nd}$ position represented in SEQ ID NO:2 of the Sequence Listing) was linked to the 5' side of the artificially synthesized gene for WTI-1b. The resulting base sequence is shown in SEQ ID NO:4.

EXAMPLE 2

Amplification of the Artificially Synthesized Gene for WTI-1b by PCR Method

Based on a sequence of 150 bp positioned in the vicinity of the center of the artificially synthesized gene for WTI-1b designed in Example 1, 80 mer HPLC grade primers 1 and 2 (SEQ ID NO:5 and SEQ ID NO:6) designed so as to overlap each other by 10 mer at 3' sides thereof were synthesized by a conventional method (see "PCR Experimental Protocol for Plant", compiled under the supervision of Ko Shimamoto and Takuji Sasaki, SHUJUNSHA Co., Ltd.). The first PCR (Program Temp. Control System PC-700, ASTEC Co., Ltd.) was performed using the two primers, each employing the other primer as a template, thereby obtaining double-stranded DNA. The reaction mixture and reaction conditions were as follows:

| (Reaction mixture) | |
|---|---|
| 5' primer 1 50 pico mole (pmol)/micro liter (μl) | 1 μl |
| 3' primer 2 50 pmol/pl | 1 μl |
| 10 × Taq buffer | 10 μl |
| 2.5 mM dNTP mix. | 8 μl |
| Taq DNA polymerase (5 unit(U)/μl)) | 1 μl |
| DDW | 79 μl |
| Total | 100 μl |
| (Reaction conditions) | |
| 94° C. | for 2 minutes |
| 37° C. | for 10 minutes |
| 30 cycles of the following set: | |
| 94° C. | for 30 seconds |
| 55° C. | for 30 seconds |
| 74° C. | for 2 minutes. |

The second PCR was performed under the same conditions as those of the first PCR except for the use of 1 μl of the first PCR product as a template and the 80 mer primers 3 and 4 (SEQ ID NO:7 and SEQ ID NO:8). These primers 3 and 4 were synthesized by a conventional method so that each of the primers respectively overlaps with the template by 10 mer at the 3' side thereof. Subsequently, using 1 μl of the second PCR product as a template, the third PCR was performed with primers 5 and 6 (SEQ ID NO:9 and SEQ ID NO:10) in the same manner as in the second PCR. Furthermore, using 1 μl of the third PCR product as a template, the fourth PCR was performed with primers 7 and 8 (SEQ ID NO:11 and SEQ ID NO:12), thereby synthesizing DNA corresponding to the DNA sequence encoding an amino acid sequence of WTI-1b protein. Herein, in order to link a signal peptide at the 5' side of the synthesized DNA, the primer 8 included a region of a 10 mer from the DNA sequence encoding WCI-3 signal peptide at the 5' side. In addition, for the later-performed cloning, the primer 7 included a SacI restriction site at the 3' side of a termination codon. The fourth PCR product was purified using a conventional method (hereinafter, referred to as a "PCR purified product A).

In addition to the series of PCRs described above, PCR was performed with primers 9 and 10 (SEQ ID NO:13 and SEQ ID NO:14) employing cDNA (SEQ ID NO:2) for WCI-3 which was subcloned between BamHI restriction site and SacI restriction site of pUC119 as a template. Reaction reagent and reaction conditions were the same as those described above. Herein, the primer 9 is a sequence which stretches over the WCI-3 signal peptide coding region and the WTI-1b protein coding region and overlaps by 15 mer, respectively. The primer 10 is a sequence corresponding to 20 mer toward the 3' side from HindIII (−240 bp) in a multi-cloning site of pUC119. The thus obtained PCR product was subjected to electrophoresis on a 1% agarose gel, thereby cutting a band having a length of interest out from the gel. The PCR product was purified by a conventional method (hereinafter, referred to as a "PCR purified product B").

PCR was performed in the above-described manner with the primers 7 and 10 (SEQ ID NO:11 and SEQ ID NO:14) using 1 μl of the PCR purified product A and 1 μl of the PCR purified product B. After the resulting product was subjected to a restriction enzyme treatment using BamHI and SacI, the resulting digested product was subcloned into pUC119. A sequence of the gene synthesized in the above-described manner was confirmed by a DNA sequencer (ABI PRISM 377 DNA Sequencer, produced by Applied Biosystems). A wrong sequence was corrected by a conventional PCR method using a primer synthesized for the wrong portion.

EXAMPLE 3
Construction of an Expression Vector

The artificially synthesized gene produced in Example 2 was cleaved at the restriction sites of BamHI and SacI of pUC119. Then, the cleaved fragment was linked to a high expression pBI-type vector (pMLH7133) (Mitsuhara et al., *Plant Cell Physiol.* 37 (1): pp. 49–59, 1996) pretreated with the BamHI and SacI restriction enzyme and ligase. *Escherichia coli* (hereinafter, referred to as "*E. coli*") (JM109) was transformed with the thus obtained construction, thereby obtaining pMLH7113mwti1b (see FIG. 5).

EXAMPLE 4
Introduction of an Expression Vector into Rice (1) Transformation of *Agrobacterium tumefaciens* EHA101

The transformation of *Agrobacterium tumefaciens* EHA101 (E. Hood et al., *Journal of Bacteriology*, pp. 1291–1301 (1986)) was performed as follows (see *Plant Molecular Biology Manual*, A3/7–8, edited by S. B. Gelven, R. A. Schilperoort and D. P. S. Verma, Kluwer Academic Publishers). EHA101 was cultured in a medium (YEP) containing 50 micro gram/milli liter ($\mu$g/ml) of kanamycin at 28° C. for 3 days. Then, a single colony was cultured in a YEP liquid medium containing no antibiotics, thereby producing a competent cell of Agrobacterium. The competent cell of Agrobacterium was transformed with pMLH7133mutilb using a Freeze-thaw method (*Plant Molecular Biology Manual*, A3/7–8, edited by S. B. Gelven, R. A. Schilperoort and D. P. S. Verma, Kluwer Academic Publishers). By culturing the transformed Agrobacterium on a medium containing 50 $\mu$g/ml kanamycin and 50 $\mu$g/ml hygromycin, a single colony was obtained.

(2) Transformation of Rice

The transformation of rice was performed in accordance with a method described in Plant Cell Technology Series 4 "Experimental protocol for model plant, chapter on rice and Arabidopsis" (pp. 93–98, compiled under the supervision of Ko Simamoto and Kiyotaka Okada, SHUJUNSHA Co., Ltd., published in Apr. 1, 1996).

The transformed Agrobacterium obtained in the aforementioned transformation (1) were seeded on a YEP medium; subjected to a shaking culture at 28° C. for 24 hours; and preserved at −80° C. as a 50% glycerol solution. A part of the thus obtained transformed Agrobacterium was applied to a YEP-agar medium, and cultured at 28° C. for 3 days. A part of the resulting colony of the Agrobacterium was picked up, and suspended in an AA medium. A callus of rice (cultivar: Nipponbare) was immersed in the suspension for 1 minute and cocultivated with the Agrobacterium on a agar medium, thereby infecting the callus with Agrobacteria. At Day 3, the infected callus were placed on a medium containing antibiotics to remove the Agrobacterium. The callus was then subcultured on a hygromycin selection medium every two weeks, and a transformed rice callus was selected. As a result of redifferentiation and conditionizing by a conventional method, 10 transformants were obtained.

EXAMPLE 5
Detection of an Expression of a Protein Having WTI-1b Activity in a Genetically Engineered Rice by Western Blotting Total protein extracts were prepared from the genetically engineered rice which was transformed with the resulting pMLH7113mwti1b as follows. Three hundred milli gram (mg) of leaves of the genetically engineered rice was freezed with liquid nitrogen and then ground. Thereafter, the extraction of protein was performed in 1 ml of urea/SDS buffer (containing 75 mM of Tris-Cl (pH6.8), 8 molar (M) of urea, 2.5% SDS, 7.5% 2-Mercaptoethanol, and 5 $\mu$M Leupeptin hemisulfate). A protein concentration of the thus obtained extract was measured by a Bradford method (Bradford, M. (1976) *Anal. Biochem.* 72:248). Extracted protein of an amount corresponding to 20 $\mu$g of total protein mass, and 1 ng, 2 ng and 4 ng of purified WTI-1b as controls were separated by SDS-polyacrylamide gel electrophoresis, respectively (see *Analytical Biochemistry* 166, 368–379); transferred to a PVDF film using a semidry transcription apparatus (EIDO Co., Ltd.); and reacted with an anti-WTI-1b antibody. Thereafter, a reacting band was immunochemically detected using an alkaline phosphatase conjugated antibody (Kirkegaard & Perry Laboratories, Inc.) as a secondary antibody. FIG. 6 shows the result of Western blotting on 2 plants (T10 and T33) of the genetically engineered rice plants which expressed the artificially synthesized gene for WTI-1b.

EXAMPLE 6
Evaluation of Resistance to Larvae of a Lepidopteran Harmful Insect, *Chilo Suppressalis* (Walker) in Genetically Engineered Rice As described in Example 5, of the genetically engineered rice plants which was confirmed to express WTI-1b by Western blotting, a plant which expressed WTI-1b at a high level was tested for its resistance against *Chilo suppressalis*. Specifically, T33 in which about 5 ng of expression level was confirmed, T60-1 and T56-2 in which about 2 nanogram (ng) of expression level was confirmed, and T55-2 in which about 1 ng of expression level was confirmed per 20 $\mu$g of total protein, were used. As a control, a leaf of the rice transformed with GUS gene using the same high expression vector was used. A leaf positioned immediately below a developing leaf of each of these plants was cut out in an about 3 centi meter (cm)×3 cm size, and put in a square-shaped styrol container (67×37×12.7 milli meter (mm), produced by GGJ) having a filter paper wetted with water spread on the bottom thereof. Five newly hatched larvae of *Chilo suppressalis* were put onto the cut leaf using a thin brush, and a lid of the container was put on. In order to prevent the dryness in the container, the container was sealed with a Parafilm (American National Can), and put into a Growth Cabinet, MLR350 (SANYO Co., Ltd.) at 25° C., in 16L8D (16 hour light and 8 hour dark) condition. Seven replicates were done. Once every two days, the old leaf was replaced with a new leaf in each of the containers. After 10 days, the larvae were taken out from the containers, and the total weight of the larvae per container was measured by an analytical electronic balance druggists' scales (Mettler Toledo, AG 245). However, in the case where the number of larvae per container is 2 or less, the total weight thereof may be too light to be measured. If this was the case, the weight was measured by combining with the weight of larvae in another container, and the weight was calculated from data of all such combinations. For example, in the case where 2 larvae survived in each of containers a and b, and 3 larvae survived in a container c, the total weight of larvae in the containers a and b, that in containers b and c, and that in the containers a and c are measured. Supposing that the results of the measurements were x milli gram (mg), y mg, and z mg, respectively, the weight of the larvae in the container a is given by (x−y+z)/2. The weights of larvae in the other containers can be obtained in the same manner. Taking a value obtained by dividing the total weight of larvae by the number of the larvae in each of the containers as a representative value, statistical processing was performed using this data. As a result, as shown in Table 3, the larvae of *Chilo suppressalis* which had eaten the genetically engineered plants statistically had significantly lower weights as compared to that of the control. Accordingly, it was confirmed that the expressed protein delayed the development of the larvae.

TABLE 3

Resistance to larvae of *Chilo suppressalis* in the rice genetically engineered with the artificially synthesized gene (mwti1b) encoding a trypsin inhibitor

| Name of clones | A weight of a larva at Day 10 mean ± standard error (mg) |
|---|---|
| T33 | 0.79 ± 0.16 a |
| T60-1 | 0.87 ± 0.21 a |
| T55-2 | 0.98 ± 0.04 a |

TABLE 3-continued

Resistance to larvae of *Chilo suppressalis* in the rice genetically engineered with the artificially synthesized gene (mwti1b) encoding a trypsin inhibitor

| Name of clones | A weight of a larva at Day 10 mean ± standard error (mg) |
|---|---|
| T56-2 | 1.70 ± 0.11 b |
| Control | 2.17 ± 0.06 c |

Notes:
Levels of expressions of the trypsin inhibitor (Western blotting) are about 5 ng for T33, about 2 ng for T60-1 and T56-2, and about 1 ng for T55-2 per 20 μg of total protein. It is shown that there is no significant difference at a 5% level among mean values denoted by identical alphabetical symbols (Tukey's test).

As described above, according to the present invention, a method for designing a useful gene which is expressed at a high efficiency in a useful plant is provided. Moreover, the present invention provides means for conferring a new character on a useful plant. Furthermore, an artificially synthesized gene which is expressed in a stable manner in higher plants including rice is provided according to the present invention.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An isolated nucleic acid sequence encoding a protein having trypsin inhibitor activity, comprising the base sequence represented by SEQ ID NO:4 of the Sequence Listing.

2. An isolated nucleic acid sequence comprising the sequence of SEQ ID NO:15.

3. An isolated nucleic acid sequence comprising the sequence of SEQ ID NO:16.

4. An isolated nucleic acid sequence comprising the sequence of SEQ ID NO:17.

5. A transgenic rice plant transformed with an expression vector comprising (I) SEQ ID NO:4 operably linked to a plant promoter, and (ii) a selectable marker gene.

* * * * *